United States Patent [19]

Soltesz

[11] Patent Number: 5,254,107

[45] Date of Patent: Oct. 19, 1993

[54] CATHETER HAVING EXTENDED BRAID REINFORCED TRANSITIONAL TIP

[75] Inventor: Peter P. Soltesz, Miami, Fla.

[73] Assignee: Cordis Corporation, Miami Lakes, Fla.

[21] Appl. No.: 949,742

[22] Filed: Sep. 23, 1992

Related U.S. Application Data

[63] Continuation of Ser. No. 665,298, Mar. 6, 1991, abandoned.

[51] Int. Cl.$^5$ ............................................ A61M 25/00
[52] U.S. Cl. ................................... 604/282; 604/280; 138/125
[58] Field of Search ............. 604/264, 280–282; 128/656, 658; 138/123, 125, 130, 132, 133, 155

[56] References Cited

U.S. PATENT DOCUMENTS

| | | | |
|---|---|---|---|
| 3,416,531 | 12/1968 | Edwards | 604/282 |
| 3,485,234 | 12/1969 | Stevens | 604/282 |
| 3,924,632 | 12/1975 | Cook | 604/282 |
| 4,516,972 | 5/1985 | Samson | 138/130 |
| 4,563,181 | 1/1986 | Wijayarathna et al. | 604/280 |
| 4,636,346 | 1/1987 | Gold et al. | 604/280 |
| 4,690,175 | 9/1987 | Ouchi et al. | 604/282 |
| 4,735,620 | 4/1988 | Ruiz . | |
| 4,817,613 | 4/1989 | Jaraczewski et al. | 604/282 |
| 4,899,787 | 2/1990 | Ouchi et al. | 604/282 |
| 4,955,862 | 9/1990 | Sepetka . | |
| 5,037,404 | 8/1991 | Gold et al. | 604/282 |

FOREIGN PATENT DOCUMENTS

| | | |
|---|---|---|
| 117093 | 2/1984 | European Pat. Off. . |
| 273618 | 12/1987 | European Pat. Off. . |
| 303487 | 8/1988 | European Pat. Off. . |

Primary Examiner—John D. Yasko
Assistant Examiner—Anthony Gutowski
Attorney, Agent, or Firm—Gerstman & Ellis, Ltd.

[57] ABSTRACT

A catheter comprises a flexible, plastic catheter shaft which carries an embedded fibrous, tubular reinforcement member typically of the braided type. The catheter shaft defines a first section which comprises a first plastic material and a second section abutting the first section which comprises a second plastic material having different physical properties from the first plastic material. The tubular reinforcement member comprises integral fibers that extend between, and are embedded in, the plastic of the first and second sections of the catheter shaft. Thus, the two different sections of the catheter shaft can have different physical properties while being reliably and permanently secured together not only by any bond present between the plastic portions but also because of the integral fibers extending between the two portions. Such a catheter may be made by threading preformed plastic catheter sections about the fibrous tubular reinforcement member and fusing.

11 Claims, 1 Drawing Sheet

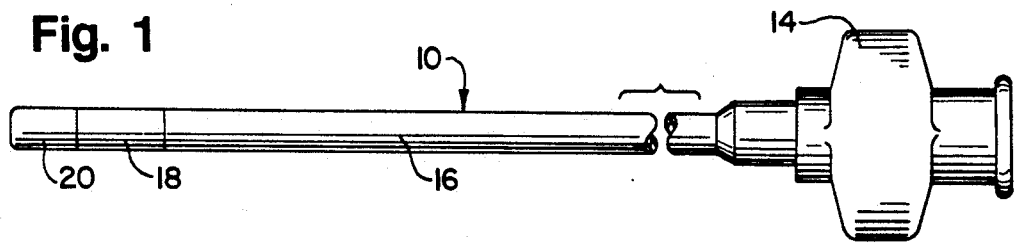
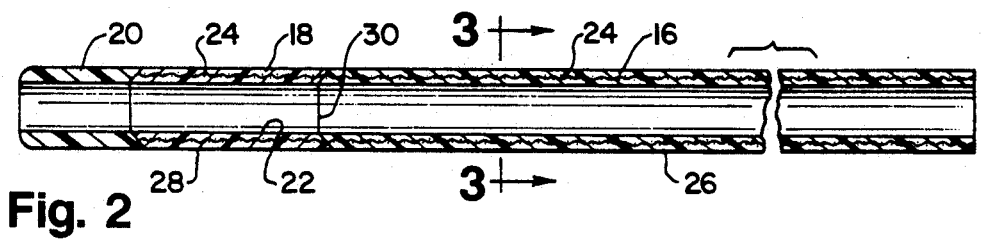
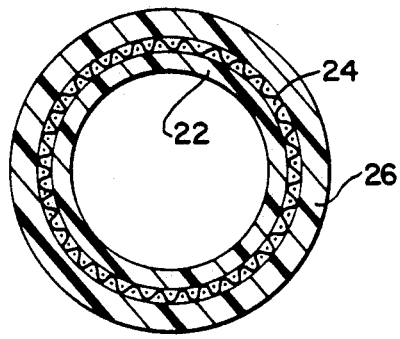
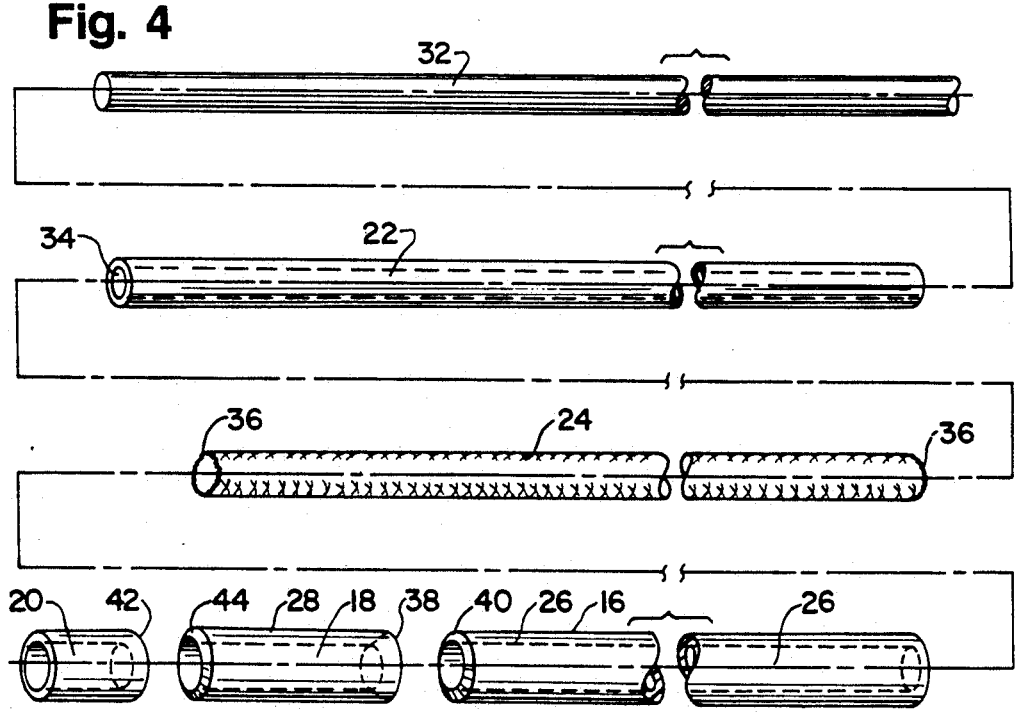

CATHETER HAVING EXTENDED BRAID REINFORCED TRANSITIONAL TIP

This is a continuation of U.S. application Ser. No. 07/665,298, filed Mar. 6, 1991 (now abandoned).

BACKGROUND OF THE INVENTION

Currently, intravascular catheters are often manufactured by forming a braided tube, typically made of stainless steel fibers or strands, over a mandrel. Often, the actual braiding takes place about an inner tube of polytetrafluoroethylene (PTFE) which, in turn, is carried on the mandrel, with the PTFE tube defining the lumen of the catheter formed by the process.

Then, after formation of the tubular braid, a plastic layer is extruded about the braided material to create the catheter body. Following this, a tubular transitional tip is sealed to one end of the catheter body. Typically, the transition tip is not reinforced with braid as is the rest of the catheter, so that the transition tip is softer and more flexible than the rest of the catheter.

Following this, in some commercial catheter designs, an added flexible tip is bonded to the free end of the tubular transition tip, with the added flexible tip containing a high loading of radiopaque agent.

For example, PTCA guiding catheters sold by The Cordis Corporation may be manufactured in this manner.

To develop large lumen catheters with a given outer diameter, the catheter wall needs to be as thin as possible. However, thin, unreinforced plastic tubing tends to kink easily, particularly where the wall thickness is less than 15 percent of the outer diameter. In order to create a flexible, yet not collapsible tubing as is needed particularly in the transitional tip area, a helical wire reinforcement has been proposed to be added to the transition tip, to provide a tubing which can have a thin wall, and can be flexible, but is resistant to collapse. The remainder of the catheter body may be reinforced with a braided tubular reinforcement. Such a proposal has been made in Castaneda et al. U.S. patent application No. 559,193, filed Jul. 27, 1990, and entitled Intravascular Catheter With Kink Resistant Tip.

In both the commercially available catheters where the tubular transition tip is unreinforced, and in the catheter of the above cited application where a helical wire reinforcement is provided, the tubular transition tip is attached to the main body of the catheter, (which typically contains a tubular, braided reinforcement) by bonding of respective ends together. Accordingly, this bond is extremely critical, since a defective bond can result in accidental separation of the transition tip from the main body of the catheter and loss thereof within a patient.

By this invention, a catheter is provided which has a catheter section such as a transition tip of significantly different physical properties from the main body of the catheter. However, despite this, there is virtually no possibility of separation of the one catheter section from the other, even if a fuse joint between the plastic of the two sections is defective. The catheters of this invention may exhibit softer, more flexible transition tips and harder, stiffer catheter main bodies, to achieve the desired characteristics of a catheter through variable physical properties along the length thereof. Likewise, the catheters of this invention can exhibit transition tips or other sections which are softer and more flexible than the catheter main body without being strongly prone to collapsing or kinking.

DESCRIPTION OF THE INVENTION

In this invention, a catheter is provided which comprises a catheter shaft. The catheter shaft carries an embedded fibrous, tubular reinforcement member, with the catheter shaft defining a first section which comprises a first plastic material and a second section abutting the first section which comprises a second plastic material having different physical properties from the first plastic material. The tubular reinforcement member comprises integral fibers that extend between, and are embedded in, the plastic of both the first and second sections of the catheter shaft. Thus, the connection between the first and second sections of the catheter shaft does not entirely depend upon a plastic bond between them, but rather the first and second catheter sections are also held together because of their embedded relation with the fibrous tubular reinforcement member, which has the integral fibers extending between and embedded in the plastic of both of the first and second sections. It follows that even in the event of a poor bond between the plastic of the first and second sections, accidental separation of the two catheter sections is essentially impossible.

Furthermore, since the first plastic material of the first section and the second plastic material of the second section have different physical properties from each other, the resulting first and second catheter sections also have different physical properties from each other. One of the catheter sections may be significantly softer and more pliable than the other of the catheter sections, depending upon the differing physical properties of the respective plastic from which they are made. For example, the first and second plastic materials may each be of a Shore D durometer that differs by at least 15 units from the other plastic material. Accordingly, one of the sections will be significantly softer than the other of the sections.

The first and second plastic materials may be elastomeric in nature, or they may be merely flexible, without the high elongation of an elastomer. Generally, plastic materials having an elongation of 100% or more are considered to be elastomers.

The fibrous, tubular reinforcement member of the catheter preferably comprises braided metal or plastic fibers, although, if desired, it may comprise one or more helical fibers which are in non-braided relation, or parallel, longitudinally directed fibers. If desired, the braided or otherwise helical fibers may vary in their angle to the axis of the catheter at various portions of the catheter along its length, to achieve differing properties of the catheter along its length due to the changing strand angles. This concept is generally taught in Gold et al. U.S. Ser. No. 270,810, now U.S. Pat. No. 5,037,404 filed Nov. 14, 1988 and entitled Catheter Having Sections of Variable Torsion Characteristics.

It may be preferred for the catheter shaft to define a third section which comprises a plastic material free of the embedded fibrous, tubular reinforcement member. Such a section may carry a high loading of radiopaque agent, in the manner of the BRITE TIP distal catheter tips on certain catheters sold by the Cordis Corporation.

Catheters in accordance with this invention may be used for any purpose, but are particularly used as intravascular catheters, for example catheters for angiography or angioplasty, particularly for use as a PTCA guiding catheter.

The catheters of this invention may be manufactured by placing a first, tubular, thermoplastic section about a fibrous, tubular reinforcement member in close contact therewith. One then places a second, tubular, thermoplastic catheter section about the fibrous, tubular reinforcement member in close contact therewith, with one end of the second catheter section at least substantially abutting an end of the first catheter section. The first and second catheter sections are made of plastic materials which have the desired different physical properties so that the resulting catheter in its sections corresponding to the first and second catheter sections exhibits differing properties in a manner corresponding to the differing properties of the thermoplastic materials used.

One fuses the first and second catheter sections to cause the first and second sections, and the fibrous, tubular reinforcement member, to form an integral, tubular mass.

The first and second catheter sections may be placed about the fibrous, tubular reinforcement member and fused in sequential order. By this invention, the order of the respective steps may be varied rather widely. Preferably, the first catheter section may be placed about the fibrous tubular reinforcement member and fused, followed by placement of the second catheter section and fusing of that section while in abutting relation with the end of the first catheter section. Alternatively, both catheter sections may be placed onto the fibrous tubular reinforcement and simultaneously fused. As an equivalent process, the first and second catheter sections may be placed inside the fibrous, tubular reinforcement member and fused together with it.

It is also preferred for the fibrous, tubular reinforcement member to be formed by winding of the fibers of the reinforcement member around a preformed, inner, tubular plastic layer carried on a mandrel, prior to placing the first and second tubular sections about the reinforcement member. Thus the reinforcement member is manufactured in situ about the inner tubular plastic layer, which plastic layer may be made of PTFE or the like.

Preferably, the fibers of the tubular reinforcement member are made of a metal such as stainless steel, and are braided. It is also preferred for the ends of the fibrous, tubular reinforcement member to be each welded into an integral, annular mass, to prevent individual fiber ends of the reinforcement member from projecting outwardly at either end. This welding step permits the use of High Tensile Strength braiding wire, which is a known and commercially available form of wire which is known to perform better than annealed braid, but has a high tendency for the wires to flair outwardly at the ends, and thus to become exposed through the walls, of the catheter which is formed around the tubular braid structure. It is of course well known that catheters which carry a supporting tubular reinforcement member typically should be manufactured with the reinforcement member being completely embedded within plastic material of the catheter, and the same is preferred for catheters of this invention.

Accordingly, by this invention a catheter may be made in which the fuse joint between the first and the second catheter sections is inseparable, even if the fuse joint is rather weak, since both the first and second catheter sections carry the same embedded, fibrous tubular reinforcement member, which serves to hold them together in virtually all circumstances. At the same time, the two catheter sections may have significantly different physical properties. Particularly, one may be softer than the other, while retaining good kink and collapse resistance due to the presence of the embedded fibrous, tubular reinforcement member. The characteristics of the fibrous, tubular reinforcement member may also be varied along the length of the catheter, for example by variation of strand angles relative to the axis of the catheter in various sections along its length.

DESCRIPTION OF THE DRAWINGS

In the drawings,

FIG. 1 is a plan view of the respective proximal and distal ends of a catheter manufactured in accordance with this invention, with a central portion omitted;

FIG. 2 is a longitudinal sectional view of the distal portion of the catheter of FIG. 1.

FIG. 3 is a transverse sectional view of the catheter of this invention taken along line 3—3 of FIG. 2; and FIG. 4 is an exploded perspective view of components of the catheter of this invention and a mandrel upon which the catheter may be manufactured, illustrative of a method of manufacturing the catheter of this invention.

DESCRIPTION OF SPECIFIC EMBODIMENT

Referring to the drawings, catheter 10 is disclosed, comprising a conventional catheter hub 14 on its proximal end, and a tubular catheter shaft which comprises a first catheter section 16, a second catheter section 18, and a distal third catheter tip section 20.

Catheter 10 comprises an inner tubular plastic layer 22 which defines the inner diameter of the catheter, and which extends in this embodiment through first and second sections 16, 18, but not through third tip section 20. Inner tubular layer 22 may be made of PTFE.

Surrounding inner plastic layer 22 is braided stainless steel fiber tubular member 24, which may be laid down about tube 22 in conventional manner with a braiding machine. Braided tubular member 24 serves as a reinforcement for the catheter, and is embedded in an outer tubular plastic layer 26 by extrusion in first catheter section 16 so that tubular reinforcement member 24 is completely buried within the plastic of layer 26 along the length of the catheter. In second catheter section 18, the same tubular reinforcement member 24 is embedded in a second outer layer of plastic 28 in a manner similar to the embedding of member 24 in plastic 26 along the length of catheter section 16.

In catheter section 16, tubular plastic material 26 may be made of a plastic material such as nylon 12, and may have a Shore D durometer of about 65 to 70, specifically a durometer of 68.

In second catheter section 18, which acts as a transition tip, the tubular plastic material 28 may also be nylon 12, but may have a Shore D durometer of about 35 to 45, specifically 40. Thus, the catheter section 18 will be substantially softer and more resilient in its "feel" than the main body of the catheter which is first catheter section 16, which main body is substantially stiffer and harder than the transition tip 18.

Catheter sections 16, 18 abut each other along line 30, and are fused together. However, their connection is not totally dependent upon the integrity of the fuse joint at line 30, since they are also held together by the single, embedded fibrous tubular reinforcement member 24.

Radiopaque catheter tip 20 may be made of a polyurethane material having a Shore A durometer of about 80, similar to the BRITE TIP catheter tip previously described. This catheter tip may carry a high loading of a radiopaque agent, to assist in fluoroscopic location of the catheter.

Thus, a catheter is provided which has a relatively soft transition tip in the manner of prior art catheters, but in which the transition tip is reinforced by the presence of the same fibrous tubular reinforcement 24 as is found in the main body of the catheter. This results in a high strength and reliable fuse joint 30 because of the presence of the continuous braid reinforcement. Also, transition tip 18 becomes kink resistant.

If desired, multiple fuse joints may be provided into catheter 10 as desired at a low cost, but with high reliability and strength by providing a continuous braid reinforcement across the fuse joints. Also, variable pitch braid may be provided to the catheter to vary the physical characteristics thereof along its length, typically by adjustment of the braiding machine a braid is laid down along the length of the catheter.

Turning to FIG. 4, an exploded view is shown for purposes of illustrating a preferred assembly method for the catheter of this invention.

A cylindrical mandrel 32 may be made of metal such as copper or, if desired plastic, with the mandrel being overcoated with a film of PTFE to provide lubricity. Thin walled (about 0.0015 inch) PTFE tubing 22 is threaded over this mandrel 32 so that mandrel 32 occupies the bore 34 of PTFE tubing 22.

Then, a tubular, braided reinforcing member 24 is applied to the exterior of tubing 22 by means of a conventional braiding machine. The resulting braided stock is removed from mandrel 32 and cut to a desired length.

If desired, at any time in the process, the respective braid ends 36 may be resistance welded (in the case that metal fiber braid is used) to fuse the ends of the fibers together into a thickened, annular weld to prevent the outward projection or flairing of individual fiber ends, as described above.

A preformed tubular plastic body 26 is then threaded over one end of tubular braid 24, and the assembly is placed into a fusing die to fuse the tubular plastic body 26 into embedded relation with braid 24. By this fusing process, molten plastic moves into the interstices between the strands of braid 24, typically into contact with the outer surface of inner PTFE layer 22, so that the braid 24 and the plastic tubing 26 becomes an integral, tubular mass. As previously stated, the material of tubing 26 may be nylon 12 having a Shore D durometer of about 68.

Then, after the first fusing step, plastic tubing section 18 may be threaded onto the assembly with its one end thereof 38 being brought into abutting relation with end 40 of tubular mass 26, while surrounding a portion of braid 24 which is not carrying tube 26. This assembly is then placed into a fusing die, and a similar fusing step takes place to cause the plastic of tube 18 to migrate into the interstices between the strands of braid 24 to join the integral, tubular mass.

At any point it may be desired to trim the braid to desired length, generally prior to the step of welding ends 36.

Finally, preformed plastic tip 20 may be applied at one end 42 to the other end 44 of what is now second tubular thermoplastic catheter section 18. This application step may be by conventional fusing of the two ends together.

Thus, by the above process, or by processes with equivalent steps and variations, the catheter of FIGS. 1–3 may be manufactured to achieve the advantages described above.

The above has been offered for illustrative purposes only, and is not intended to limit the scope of the invention of this application, which is as defined in the claims below.

That which is claimed is:

1. An intravascular catheter which comprises:
   a flexible, plastic inner tube; a fibrous, tubular reinforcement member carried by said inner tube;
   a first section comprising a first plastic material overlying said inner tube and reinforcement member;
   a second section comprising a second plastic material having different physical properties from said first plastic material and overlying said inner tube and reinforcement member;
   said first section being in abutting relationship which said second section;
   said tubular reinforcement member comprising integral fibers that extend between and are embedded in the plastic of both said first and second sections; and
   a third section abutting said second section, said third section comprising a plastic free of said embedded, fibrous, tubular reinforcement member and generally free of said inner tube;
   said catheter having a central, smooth, plastic-walled open lumen.

2. The catheter of claim 1 in which said fibrous, tubular reinforcement member comprises braided fibers.

3. The catheter of claim 1 in which said first and second plastic materials are nylon.

4. The catheter of claim 1 in which said first and second plastic materials are each of a Shore D Durometer that differs by at least 15 units from the other.

5. The catheter of claim 1 in which said reinforcement member comprises metal fibers, said reinforcement member defining annular, integral, welded ends free of outwardly projecting individual fibers.

6. The catheter of claim 1 in which the smooth, lumen-defining inner plastic surface is defined by said inner tube about which said embedded, fibrous, tubular reinforcement member resides.

7. The catheter of claim 6 in which said inner tube is made of polytetrafluoroethylene.

8. The catheter of claim 7 in which said first and second plastic materials are nylon, each being of a Shore D durometer that differs by at least 15 units from the other.

9. The catheter of claim 8 in which said reinforcement member comprises metal fibers, said reinforcement member defining annular, integral, welded ends free of outwardly projecting individual fibers.

10. An intravascular catheter which comprises:
    a flexible, plastic inner tube;
    a fibrous, braided tubular reinforcement member comprising metal fibers carried by said inner rube;
    a first section comprising first nylon material overlying said inner tube and reinforcement member;
    a second section comprising second nylon material having different physical properties from said first nylon material and overlying said inner tube and reinforcement member;

said first section being in abutting relationship with second section;

said tubular reinforcement member comprising integral metal braided fibers that extend between and are embedded in the nylon material of both said first and second sections;

said reinforcement member defining annular, integral, welded ends free of outwardly projecting individual fibers;

a third section abutting said second section, said third section comprising a plastic free of said embedded, fibrous, tubular reinforcement member and generally free of said inner tube; and said catheter having a central, smooth, plastic-walled, opened lumen.

11. The catheter of claim 10 in which said first and second nylon plastic materials are each of a Shore D durometer that differs by at least 15 units from the other.

* * * * *